(12) United States Patent
Wang et al.

(10) Patent No.: US 8,343,909 B2
(45) Date of Patent: Jan. 1, 2013

(54) **METHOD FOR PRODUCING *ABELMOSCHUS MANIHOT* MEDICUS FLOWER PERFUMED PRODUCT**

(75) Inventors: Zhiyuan Wang, XingTai (CN); Shaozhang Wang, XingTai (CN)

(73) Assignee: Beijing Dongsheng Agricultural Technology Development (Group) Co., Ltd., Beijing (CN)

( * ) Notice: Subject to any disclaimer, the term of this patent is extended or adjusted under 35 U.S.C. 154(b) by 0 days.

(21) Appl. No.: 13/543,823

(22) Filed: Jul. 7, 2012

(65) Prior Publication Data

US 2012/0276231 A1    Nov. 1, 2012

Related U.S. Application Data

(63) Continuation of application No. 12/739,405, filed as application No. PCT/CN2007/070932 on Oct. 22, 2007, now abandoned.

(51) Int. Cl.
*A61Q 13/00*   (2006.01)
*C11B 9/00*    (2006.01)

(52) U.S. Cl. ............................................. 512/5; 512/1
(58) Field of Classification Search .................. 514/5, 1; 424/725

See application file for complete search history.

(56) References Cited

U.S. PATENT DOCUMENTS

2010/0311951 A1 *  12/2010  Wang et al. .................... 530/370

FOREIGN PATENT DOCUMENTS

| CN | 1105059     | * | 7/1995 |
| CN | 101002536 A |   | 7/2007 |

OTHER PUBLICATIONS

Committee on specifications, Food Chemicals Codex of the Committee on Food Protection, National Research Council: Food Chemical Codex; 1972, p. 4.*

Lake, Jane: Homemade Bath Oil With Fragrant Potpourri; allfreegifts.com [online] URL http://www.allfreecrafts.com/giftinajar/homemad-bath-oil.shtml> 2 pages, archived to Dec. 14, 2005.*

* cited by examiner

*Primary Examiner* — Patricia Leith
(74) *Attorney, Agent, or Firm* — Cheng-Ju Chiang

(57) ABSTRACT

A producing method of *Abelmoschus manihot* Medicus flower perfumed products comprises steps of choosing a carrier from one of *Abelmoschus manihot* Medicus oil, vegetable oil with unsaturated fatty acid more than 60% and acid value less than 4.0, and cosmetic base oil grade high purity mineral oil; choosing *Abelmoschus manihot* Medicus flowers as main ingredient flowers; immersing the main ingredient flowers in the carrier by immersing the main ingredient flowers below a liquid level of the carrier; and placing stationarily the carrier with the main ingredient flowers immersed therein in dark places and keeping the carrier out of any direct sunlight under an environment with a temperature between 18 degrees centigrade and 48 degrees centigrade for more than 6 hours, or a temperature below 18 degrees centigrade for more than 180 hours.

5 Claims, No Drawings

US 8,343,909 B2

METHOD FOR PRODUCING *ABELMOSCHUS MANIHOT* MEDICUS FLOWER PERFUMED PRODUCT

CROSS REFERENCE TO RELATED APPLICATIONS

The present application is a continuation of a U.S. patent application Ser. No. 12/739,405, filed on Apr. 22, 2010 now abandoned, which is a 35 U.S.C. §371 National Phase conversion of International (PCT) Patent Application No. PCT/CN2007/070932, filed on Oct. 22, 2007 and published in Chinese. The disclosure of both of the above identified patent applications are incorporated by reference herein.

FIELD OF THE INVENTION

The present invention belongs to the plant development field and relates to a kind of primitive nutritional supplement or corresponding medicinal materials and method for producing the same.

BACKGROUND OF THE INVENTION

*Abelmoschus manihot* (Linn.) Medicus is a kind of herbs belonging to Abelmoschus of Malvaceae. Its code in China National Standard GB/T14467-93, implemented from Jan. 1, 1994, is 6000010003. In the document with the China Patent Publication Number CN101002536A, Hibiscus manihotis an optimally selected population of *Abelmoschus manihot* (Linn.) Medicus. Many documents and published papers on the development of the flower of this plant all claim that the flower is nontoxic. An important document on the *Abelmoschus manihot* (Linn.) Medicus flower is "Studies on the Chemical Constituents of *Abelmoschus manihot*", written by Cao, Yongxiang from Xi'an Jiaotong University, with its CLC being R282.71 and 8284.2, and IEEE-IEL being Y454247. In the document, it mentioned that the active ingredient in *Abelmoschus manihot* (Linn.) Medicus lies in the volatile substance and gas chromatography-mass spectrometry was used to determine 11 compounds in the volatile substance. When separating aglycone from the part of ether, the author found that a high content substance is very unstable and can not be separated out all the time. Owing to the aqueous alcohol used in the recrystallization process, and heat exposure during the storage and heating during the EI-MS assaying, the structure of other samples can not be identified.

When making *Abelmoschus manihot* (Linn.) Medicus flower products, the inventor can smell the strong fragrance of the *Abelmoschus manihot* (Linn.) Medicus flower in the whole workshop and those who experienced all have rather deep impression. However, it is hard to smell the faint fragrance during the packaging, storage and transportation, and using. According to present documentaries and existing technologies, it is difficult to reserve and use the volatile substances in *Abelmoschus manihot* (Linn.) Medicus flowers. Concerning the theme ideas, product proposal and technology design of the present invention, there is no any other one alike.

SUMMARY AND CONTENT OF THE INVENTION

The objective of the invention is to seek suitable carrier for the volatile substance in *Abelmoschus manihot* (Linn.) Medicus flower and solve the problem that the volatile substance can not be separated out and reserved for use, so as to provide a kind of edible or external raw material products for the health care industry.

The implementation of the invention is to immerse the *Abelmoschus manihot* Medicus flower or dried *Abelmoschus manihot* Medicus flower or *Abelmoschus manihot* Medicus tissue fragments in *Abelmoschus manihot* Medicus oil, or vegetable oil with more than 60% unsaturated fatty acid, or cosmetic base oil grade mineral oil. Then the oil is stored in shade and applied as edible or external raw materials.

The optimal selection of the above mentioned *Abelmoschus manihot* Medicus is the Hibiscus manihot population of *Abelmoschus manihot* (Linn.) Medicus, mentioned in the BACKGROUND OF THE INVENTION.

The specific procedures are:

1. Choose the carrier: *Abelmoschus manihot* Medicus oil, or vegetable oil with unsaturated fatty acid more than 60% and acid value less than 4.0, or cosmetic base oil grade high purity mineral oil. It is called carrier oil.

2. Choose the *Abelmoschus manihot* Medicus flower: fresh entire flower, or dried entire flower, or fragments of fresh *Abelmoschus manihot* Medicus flower tissues, or fragments of dried *Abelmoschus manihot* Medicus flower tissues. It is called main ingredient flower.

3. The above mentioned main ingredient flower is immersed in the carrier. Here the concept of immersion means that the main ingredient flower is immersed below the carrier liquid level and there is no main ingredient flower above the liquid level of the carrier. The material going through the treatment is the raw meal of the product.

4. The above mentioned raw meal is kept out of the direct sunlight, or after shaking or stirring. The shaking frequency is less than 230 times per minute. The stirring speed is less than 380 rounds per minute. Both shaking and stirring time is more than 3 minutes. The material going through this treatment is called clinker of the product.

5. When the above mentioned clinker is placed under an environment with the temperature between 18 degrees centigrade and 48 degrees centigrade, the subpackage and application is conducted after stored more than 6 hours. When the environmental temperature is below 18 degrees centigrade, the storage period shall be more than 180 hours before subpackage and application.

6. The above mentioned raw meal and clinker in the product of the present invention are used for food and medicine as raw materials. And the *Abelmoschus manihot* Medicus flower perfumed product with mineral oil as the carrier is used as raw material for medicine, skin care and hair care industries.

The present invention product makes the volatile substance in the *Abelmoschus manihot* Medicus flower effectively stored in fat carrier. The production and application practice of the product proved the anti-oxidation effect of the volatile substance in the *Abelmoschus manihot* Medicus flower and the natural bioflavonoid, by significant oxidation resistance of the fat. So utilizing the edible vegetable oil with high content of unsaturated fatty acid as the carrier can keep the fat unchanged for many years.

Product of the present invention has no any artificially synthetic preservative added during the making, storage and transportation process and keeps the combination state of 100% natural substance. Being the raw material, it provides the maximum selection space for its application. The fat carrier of the present invention product has a much higher boiling point. For example, the boiling point of the *Abelmoschus manihot* Medicus oil is 180 degrees centigrade. The volatile substance exists in it is much more stable, with nearly no escape. The invention is a better selection under the present technology condition and provides a good footstep for the development of relevant technology.

The optimal selection of the above mentioned *Abelmoschus manihot* Medicus is the Hibiscus manihot population of *Abelmoschus manihot* (Linn.) Medicus, mentioned in the BACKGROUND OF THE INVENTION.

BENEFICIAL EFFECTS

The present invention effectively keeps the natural state of over 10 kind active ingredients in *Abelmoschus manihot* (Linn.) Medicus flower, so as to give play to the efficacy of the active ingredients in application. Relevant effects of the product of the present invention in application are rather obvious and easy to be verified. For example, Professor Yang, Yongnian from the Science and Technology Development Department of Beijing University got the present invention products from the inventor for many times for a period of one year and used them for aged health care and on Parkinson's Disease patients, finally achieved very good effect in application.

DETAILED DESCRIPTION OF EMBODIMENTS OF THE INVENTION

The implementation of the invention is to immerse the *Abelmoschus manihot* Medicus flower or dried *Abelmoschus manihot* Medicus flower or *Abelmoschus manihot* Medicus tissue fragments in *Abelmoschus manihot* Medicus oil, or vegetable oil with more than 60% unsaturated fatty acid, or cosmetic base oil grade mineral oil. Then the oil is stored in shade and applied as edible or external raw materials.

The optimal selection of the above mentioned *Abelmoschus manihot* Medicus is the Hibiscus manihot population of *Abelmoschus manihot* (Linn.) Medicus, mentioned in the BACKGROUND OF THE INVENTION.

The following specific procedures are used for the invention:

1. Choose the carrier: *Abelmoschus manihot* Medicus oil, or vegetable oil with unsaturated fatty acid more than 60% and acid value less than 4.0, or cosmetic base oil grade high purity mineral oil. It is called carrier oil.

2. Choose the *Abelmoschus manihot* Medicus flower: fresh entire flower, or dried entire flower, or fragments of fresh *Abelmoschus manihot* Medicus flower tissues, or fragments of dried *Abelmoschus manihot* Medicus flower tissues. It is called main ingredient flower.

3. The above mentioned main ingredient flower is immersed in the carrier. Here the concept of immersion means that the main ingredient flower is immersed below the carrier liquid level and there is no main ingredient flower above the liquid level of the carrier. The material going through the treatment is the raw meal of the product.

4. The above mentioned raw meal is kept out of the direct sunlight, or after shaking or stirring. The shaking frequency is less than 230 times per minute. The stirring speed is less than 380 rounds per minute. Both shaking and stirring time is more than 3 minutes. The material going through this treatment is called clinker of the product.

5. When the above mentioned clinker is placed under an environment with the temperature between 18 degrees centigrade and 48 degrees centigrade, the subpackage and application is conducted after stored more than 6 hours. When the environmental temperature is below 18 degrees centigrade, the storage period shall be more than 180 hours before subpackage and application.

6. The above mentioned raw meal and clinker in the product of the present invention are used for food and medicine as raw materials. And the *Abelmoschus manihot* Medicus flower perfumed product with mineral oil as the carrier is used as raw material for medicine, skin care and hair care industries.

EMBODIMENT

Embodiment 1

Choose 100 kg fresh Hibiscus manihot flower of the *Abelmoschus manihot* (Linn.) Medicus species, and 300 kg fat content of the above mentioned Hibiscus manihot. The main ingredient flower and carrier oil are placed together in a porcelain jar. As Hibiscus manihot flower suspends in the oil, higher than the liquid level, a stainless steel flute is placed on the suspension plane above the oil level. Then apply force on the stainless steel flute, to make the Hibiscus manihot flower fully immersed in the Hibiscus manihot oil below the oil level, for use as food or medicinal materials.

Embodiment 2

Keep the state of the materials made from the above embodiment 1 and pressurize them for over 12 hours. As the environmental temperature at that time is 17 degrees centigrade, the immersion oil is kept the above pressure state, covered for store and placed in shade for one month before direct subpackage and application.

Embodiment 3

Choose 50 kg fragments of dried *Abelmoschus manihot* (Linn.) Medicus flower tissues and 50 kg medical paraffin oil as main ingredient flower. Put the main ingredient flower and carrier oil in a reaction vessel with shaking and stirring function. First shake them for 6 minutes with the frequency of 108(+/−1) times per minute, stir them for 3 minutes at the speed of 180 rounds per minute, then place them in a stainless steel jar and finally conduct subpackage and application after three days' storage in dark place.

Embodiment 4

Choose 100 kg dried *Abelmoschus manihot* (Linn.) Medicus entire flower and 100 kg edible tea oil as main ingredient flower. Put the carrier oil of the main ingredient flower in an enamel vessel. Part of the main ingredient flower is above the oil level at this time. Place a stainless steel mesh screen on it to pressurize and make it immersed below the oil level for 3 hours and then put a small stirrer in the oil. Stir the main ingredient flower and carrier oil at a gradually increased speed from 60 rounds per minute to 180 rounds per minute for 6 minutes, take out the stirrer, seal the stainless steel vessel and conduct subpackage for application after 6 hours' storage in dark place at the normal temperature of 33 degrees centigrade.

What is claimed is:

1. A method for producing an *Abelmoschus manihot* Linn. Medicus flower perfumed product, comprising:
choosing a carrier from one of *Abelmoschus manihot* Linn. Medicus oil, a vegetable oil with more than 60% unsaturated fatty acid and acid value less than 4.0, tea oil and a mineral oil;
choosing a main ingredient flower from one of *Abelmoschus manihot* L. Medicus fresh entire flowers, *Abelmoschus manihot* L. Medicus dried entire flowers, fragments of fresh *Abelmoschus manihot* L. Medicus flower tissues, and fragments of dried *Abelmoschus manihot* L. Medicus flower tissues;

immersing the main ingredient flower in the carrier below the liquid level of the carrier so that there is no main ingredient flower above the liquid level of the carrier; and storing the carrier, with the main ingredient flowers immersed therein, in the dark either at a temperature between 18 degrees centigrade and 48 degrees centigrade for more than 6 hours or at a temperature below 18 degrees centigrade for more than 180 hours.

2. The method according to claim 1, wherein the main ingredient flowers is 100 kg fresh *Abelmoschus manihot* L. Medicus flowers, and the carrier is 300 kg of *Abelmoschus manihot* L. Medicus manihot flower oil.

3. The method according to claim 1, wherein the main ingredient flowers is 50 kg of fragments of dried *Abelmoschus manihot* L. Medicus flower tissues and the carrier is 50 kg medical paraffin oil, wherein the main ingredient flowers and the carrier are placed in a reaction vessel with shaking and stirring capabilities and firstly shaken for 6 minutes then stirred for 3 minutes at a speed of 180 revolutions per minute, and wherein the shaken and stirred product is placed in a stainless steel jar for three days in the dark.

4. The method according to claim 1, wherein the main ingredient flowers is 100 kg dried *Abelmoschus manihot* L. Medicus entire flower and the carrier is 100 kg tea oil, wherein the main ingredient flowers and the carrier are placed in an enamel vessel and pressed by a stainless steel mesh screen to immerse the main ingredient flowers below the liquid level of the carrier for 3 hours, collecting the resulting mixture and stirring the mixture with a stirrer from 60 revolutions per minute to 180 revolutions per minute for 6 minutes, and wherein the stirred mixture is sealed in a stainless steel vessel for 6 hours in the dark at a temperature of 33 degrees centigrade.

5. The method according to claim 1, wherein the carrier with the main ingredient flowers immersed therein is shaken or stirred before being placed in the dark, wherein the stirring speed is less than 380 revolutions per minute, and wherein the shaking or stirring time is carried out for more than 3 minutes.

* * * * *